(12) United States Patent
Chang et al.

(10) Patent No.: US 6,557,416 B2
(45) Date of Patent: May 6, 2003

(54) HIGH RESOLUTION BIOSENSOR SYSTEM

(75) Inventors: I-Nan Chang, Taipei (TW); Chung Chih Lo, Taipei (TW); Wu Chin Chen, Taipei (TW); Yen-Wen Chen, Taipei (TW)

(73) Assignee: ANT Technology Co., Ltd., Taipei (TW)

( * ) Notice: Subject to any disclaimer, the term of this patent is extended or adjusted under 35 U.S.C. 154(b) by 0 days.

(21) Appl. No.: 09/801,777

(22) Filed: Mar. 9, 2001

(65) Prior Publication Data

US 2001/0027685 A1 Oct. 11, 2001

(30) Foreign Application Priority Data

Mar. 31, 2000 (TW) ................................. 89209330 U

(51) Int. Cl.$^7$ ..................... G01N 33/48; G01N 33/497
(52) U.S. Cl. ................. 73/579; 73/23.3; 73/24.03; 73/32 A; 73/64.53
(58) Field of Search ............... 73/579, 23.31, 73/23.32, 23.33, 24.03, 32 A, 61.75, 61.79, 64.53, 23.3; 327/156, 160, 159; 331/1 R

(56) References Cited

U.S. PATENT DOCUMENTS

| | | | |
|---|---|---|---|
| 4,789,804 A | * 12/1988 | Karube et al. | 310/311 |
| 4,801,897 A | * 1/1989 | Flecken | 331/155 |
| 5,095,263 A | * 3/1992 | Peters | 324/166 |
| 5,281,863 A | * 1/1994 | Bond et al. | 327/105 |
| 5,594,163 A | * 1/1997 | Suzuki | 73/61.44 |
| 5,817,940 A | * 10/1998 | Kobayashi et al. | 73/504.12 |
| 6,150,857 A | * 11/2000 | Blaser | 327/156 |

FOREIGN PATENT DOCUMENTS

JP           4-244944     * 9/1992    ............ G01N/5/02

* cited by examiner

*Primary Examiner*—Daniel S. Larkin
*Assistant Examiner*—Rose M. Miller
(74) *Attorney, Agent, or Firm*—Bacon & Thomas

(57) ABSTRACT

A high resolution biosensing system for detecting and identifying a biochemical material to be tested by using proportional relationship between frequency variation of oscillation and mass of the biochemical material to be tested comprises a biosensor; an oscillator for generating oscillation based on the sensed result; a phase-lock loop circuit receiving the oscillation of the oscillator and generating pulse signals; an ultra-high frequency counter for counting the pulse signals; and a microprocessor for storing and displaying output from the ultra-high frequency counter and for controlling the oscillator. The phase-lock loop circuit generates the pulse signals of a frequency, which is n times the frequency of the oscillator and with a constant phase difference therebetween to trigger the ultra-high frequency counter. Accordingly, the resolution can be raised up to n times.

2 Claims, 4 Drawing Sheets

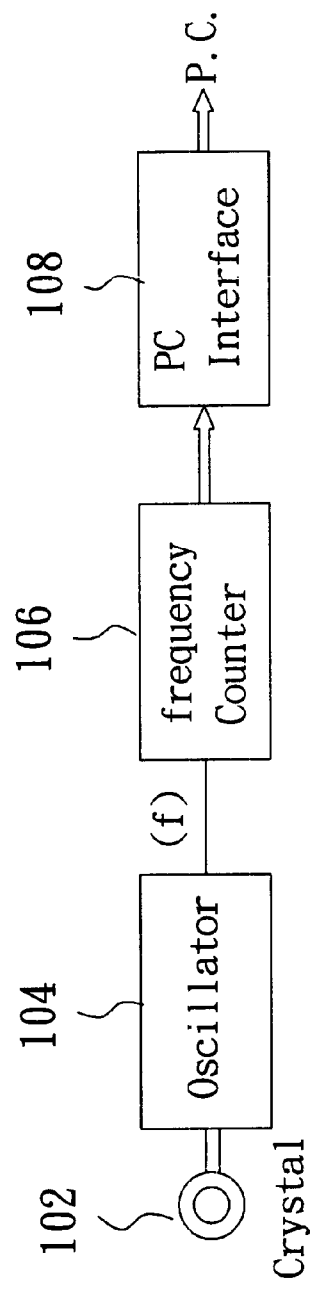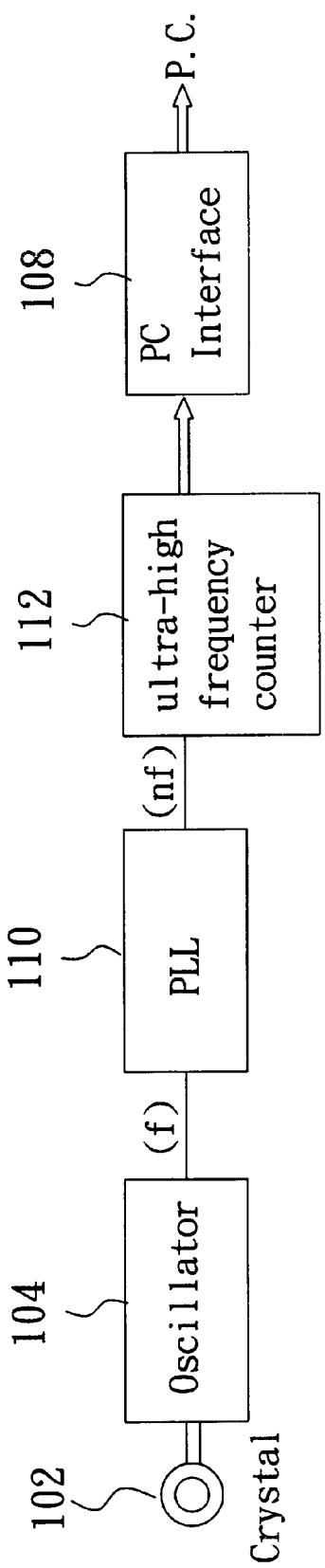

*Z stands for phase lag, a fixed value.
*As n=4, (nf) is 4 times f, while the phase lag Z is fixed.

HIGH RESOLUTION BIOSENSOR SYSTEM

BACKGROUND OF TECHNOLOGY

In the fast developing field of biology and medical technology, it is an obstacle to the advancement that people cannot precisely measure the variation of biological phenomenon in real time to realize the function of the variation. Since 1990, a biosensor system has been defined as an apparatus which utilizes immobilized biomolecules in combination with a transducer to detect in vivo or in vitro chemicals or produce a response after a specific interaction with the chemicals. The biomolecules comprise molecule identifying elements for the tissue of an organism or an individual cell. Such elements are used for receiving or generating biosensor signals. The transducer is a hardware instrument element that mainly functions as a physical signal converting element. Consequently, a biosensor system can be constituted by combining specific biologically active materials, which can be obtained by isolating, purifying or inventively synthesizing the materials via biochemical methods, with a precise and fast responding physical transducer.

An earlier biosensor, which was constituted by an enzyme electrode such as the enzyme electrode for use in the blood-sugar test (Clark et al., 1962), was developed and marketed by the YSI Company. Since 1988, pen-shaped and card-shaped enzyme electrodes utilizing a mediator to speed up the time of response, enhance the sensitivity, and reduce the interference caused by other biological materials, have also been developed (Demielson et al., 1988). However, the sensitivity of such first generation biosensors is limited by the weak conjugation between the biomolecule-enzyme and the test target. Even though the enzyme possesses the ability to amplify the signal, there still exists a defect in which a test target of low concentration cannot be detected in a short period of time.

The second generation biosensor, which is an affinity biosensor, is designed to overcome the above-described obstacles. It adopts an anti-body or receptor protein as a molecule identifier. Generally, its conjugation constant between biomolecules and target molecules is above $10^7$ $M^{-1}$, and its detectable limit value is much more precise and smaller than that of the first generation biosensor.

The transducer of the second generation biosensor can be made of a field effect transistor (FET), a fiber optic sensor (FOS), a piezoelectric crystal (PZ), a surface acoustic wave (SAW) device, etc. The second generation biosensor was developed by a Swedish company, Pharmacia Biosensor AB, in the year 1991 by employing the technologies of micromachining and genetic engineering to develop the affinity biosensors, BIACORE and BIA lite. These products utilize the technologies of surface plasmon resonance (SPR) and micromachining to conduct a real time detection of biomolecules, in general, under the concentration from $10^{-3}$ g/ml to $10^{-9}$ g/ml to achieve an acceptable resolution. Although these products may achieve high resolution, they are not economical and practical because of their difficult technologies and their high price, for example, US $300,000 dollars. In addition, the price of their consumable detection chips, which cost $200 US dollars for each chip, is also very expensive. As a result, it is quite difficult to popularize these products.

Among the second generation biosensors, an alternative one adopts a quartz crystal microbalance (QCM) system using piezoelectric technology as the transducer. Such an apparatus, which costs about $30,000 US dollars and each consumable chip of which costs about $30 US dollars, is much cheaper than that of the aforesaid one, which utilizes the technology of SPR. However, its resolution and sensitivity can merely reach $10^{-3}$ g/ml to $10^{-6}$ g/ml.

SUMMARY OF THE INVENTION

An object of the present invention is to overcome the defect of QCM, and promote the sensitivity and resolution of the QCM biosensor system, in order to make it more economical and practicable. Furthermore, if the present invention is utilized in combination with a transducer of high precision, the detection resolution can be significantly raised.

In accordance with the present invention, a high resolution biosensor system measures the effects of gas or liquid characteristics, such as density, viscosity and temperature of the gas or liquid present at the surface of a piezoelectric quartz crystal, as well as the differential pressure between the two sides of the crystal, on the oscillation frequency of the crystal. The relation among these factors can be illustrated by the following equation:

$$\Delta F = CF^2 \Delta M/A + CF^{2/3}(\Delta \eta_L \Delta \rho_L)^{1/2}$$

wherein

C: a constant, $-2.3 \times 10^{-6}$ cm$^2$/Hz-g $\Delta F$: the frequency variation caused by mass load F: oscillation frequency of quartz crystal $\Delta M$: the variation of mass load carried by the electrode A: area of electrode $\Delta \eta_L$: variation of solution viscosity $\rho_L$: variation of solution density As the density and viscosity of the solution remain constant, the frequency variation ($\Delta F$) is directly proportional to the variation of the mass load ($\Delta M$). However, the precision of the frequency counter used in traditional biosensor systems can only reach 1 Hz. If the base clock is 10 MHz, the ultimately detectable limit can only be $0.43 \times 10^{-9}$ g (approximately corresponding to $4.3 \times 10^{-6}$ g/ml). The present invention utilizes a phase-lock loop (PLL) circuit to generate a counting signal that has the same phase as the base clock, but the frequency thereof is n times higher than that of the base clock, such that the resolution can be raised n times. For instance, if n=100, the frequency for the resolution can reach 0.01 Hz and the ultimately detectable limit can be up to $4.3 \times 10^{-12}$ g (approximately corresponding to $4.3 \times 10^{-9}$ g/ml). This invention may vastly enhance the precision of measurement and improve the identification sensitivity of biological target by up to 100 times, and thus reach the virus level of identification. Furthermore, the PLL circuit comprises a filter for tracing phase error, and utilizes a closed loop servo control to maintain the phase relation. Therefore, the frequency jittering problem customarily caused by noises in input signals can be overcome, because the output signal of PLL does not disappear with the instantaneous variation, such that the S/N ratio can be raised and a stable output frequency can be achieved.

BRIEF DESCRIPTION OF DRAWINGS

FIG. 1 is schematic diagram of a conventional piezoelectric microbalance biosensor;

FIG. 2 is schematic diagram of the high resolution biosensing system according to the present invention;

DESCRIPTION OF THE INVENTION

Figure 3:
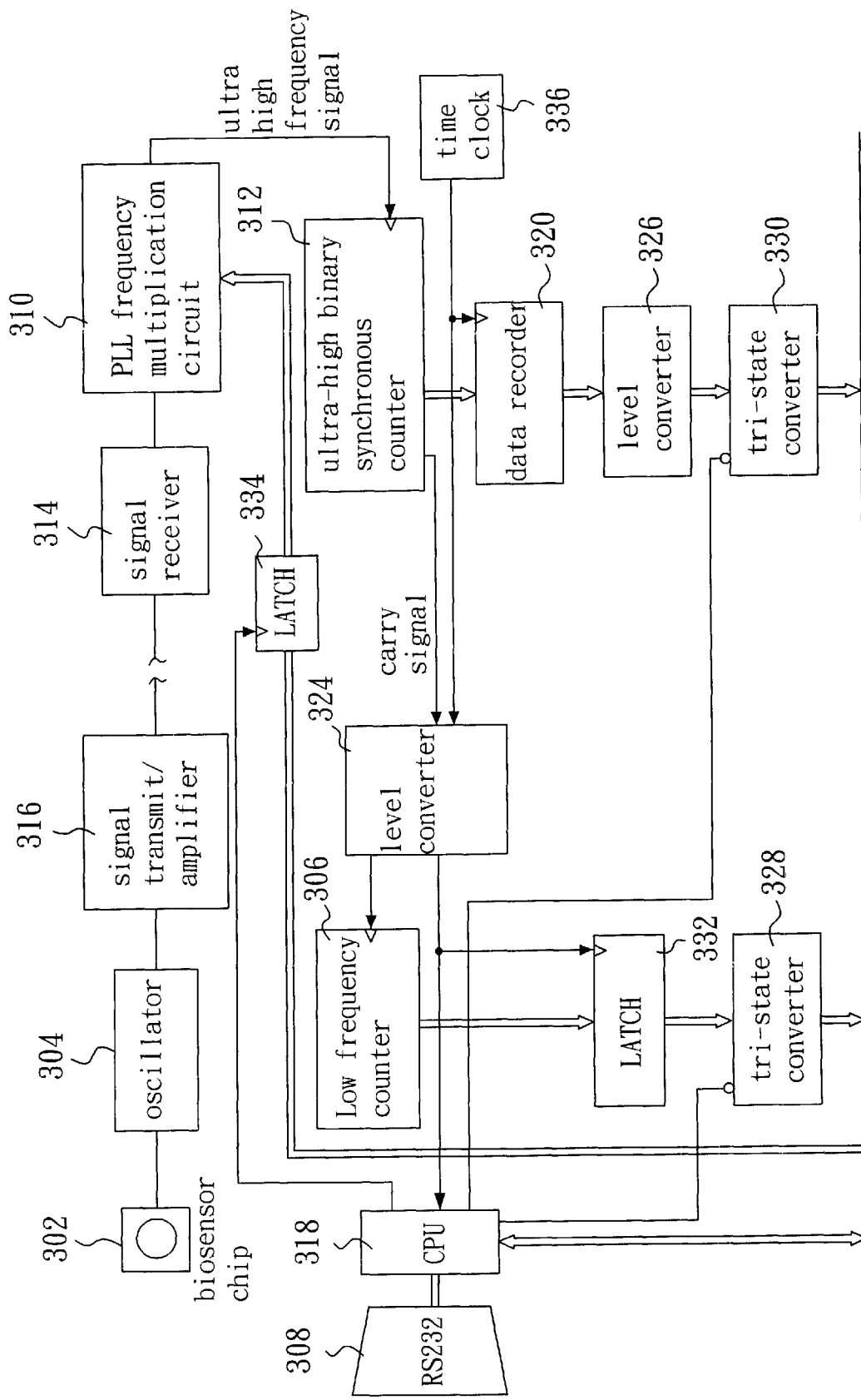
FIG. 3 shows an embodiment for practicing the concept illustrated in FIG. 2.

One of the embodiments of the present invention is a modification of a piezoelectric biosensor (100) of the type illustrated in FIG. 1, which induces an oscillating electric field along a direction perpendicular to the surface of the chip to make the crystal lattice (102) inside the chip produce mechanical oscillations similar to a standing wave. This type of mechanical oscillation can be indicated by a specific frequency. A resonant frequency can be measured by applying an appropriate oscillation circuit (104) and frequency counter (106), the resulting frequency being made available to a computer (P.C.) through an interface (108) for analysis.

The following equation shows the relationship between the frequency of the piezoelectric quartz crystal and the solution of the detected organism:

$$\Delta F = CF^2 \Delta M/A + CF^{2/3}(\Delta \eta_L \Delta \rho_L)^{1/2}$$

wherein

C: a constant, $-2.3 \times 10^{-6}$ cm$^2$/Hz-g $\Delta F$: the frequency variation caused by mass load F: oscillation frequency of quartz crystal $\Delta M$: the variation of mass load carried by the electrode A: area of electrode $\Delta \eta_L$: variation of solution viscosity $\Delta \rho_L$: variation of solution density As the density and viscosity of the solution remain constant, the frequency variation is directly proportional to the mass load, and will be detected by the QCM biological detection crystal. Then, the QCM crystal outputs a signal accordingly.

In the prior art shown in FIG. 1, the known biosensor (100) transmits the signal to oscillation circuit (104) to produce an oscillation signal, and the oscillation signal of the oscillator is transmitted to frequency counter (106) to obtain a frequency value. The principle of the counter is to sum up the counts of the input pulses every second to figure out the frequency value (the sum of pulses per second). For example, if the pulses are summed up one time per second, the minimum unit (resolution) is 1 Hz. If they are summed at ten second intervals, the minimum unit is 0.1 Hz (namely, 0.1 pulse per second). As a result, for the purpose of promoting resolution, the sampling rate must be compromised. If the sampling rate remains at one time per second, when a resolution higher than 1Hz is desired, the pulse would need to be divided into more units for counting.

The present invention provides a solution to overcome the above problem by providing a modified biosensor (101) that utilizes a phase lock loop (PLL) circuit (110) and ultra-high frequency counter (112) in place of the frequency counter (106) of the conventional biosensor (100). The PLL circuit (110) generates a signal that has the same phase as the original one but has a counting frequency which is n times the original frequency.

Figure 4:
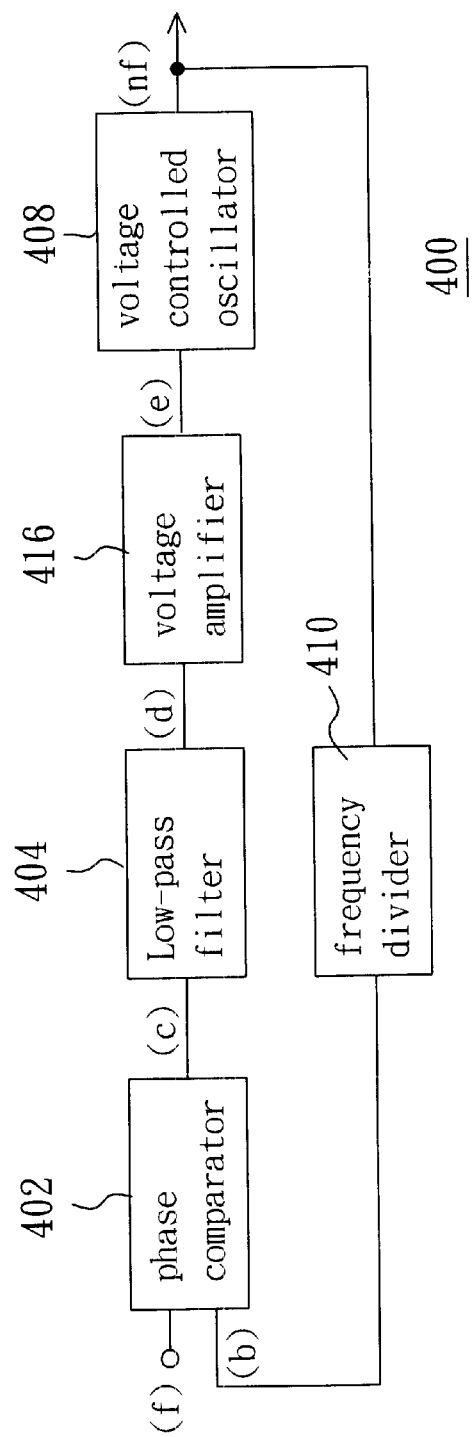
FIG. 4 is a block diagram showing the PLL circuit of the present invention.
Figure 5:
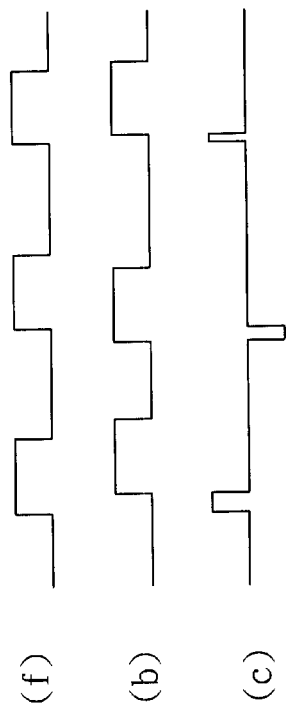
FIG. 5 is a waveform diagram for signals at each node of FIG. 4.
Figure 6:
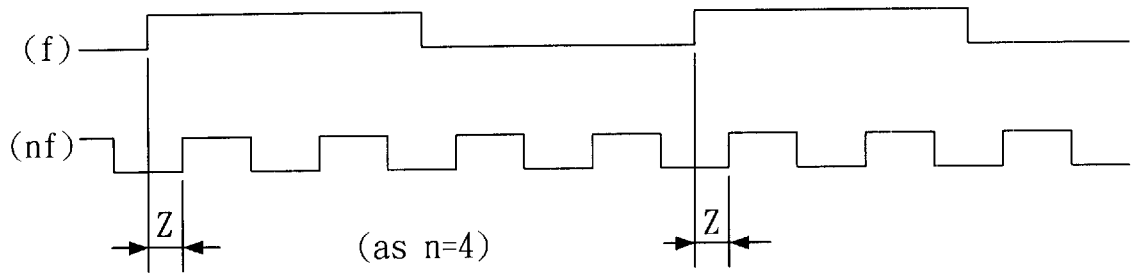
FIG. 6 illustrates the relationship between the input and the output of the PLL circuit according to the present invention.

The relation between the new counting signal and the original one is illustrated in FIG 6, while FIG. 4 shows details of the phase lock loop circuit (110). The output signal (f) of the oscillation circuit of the modified biosensor (101) is transmitted, to a phase comparator (402) having an a second input the frequency multiplied output of voltage controlled amplifier 408 for comparing the phase of signals. If the phase of the input signal (f) leads the signal at node (b), the signal at node (c) is a positive wave. The more the signal (f) leads the signal at node (b), the broader the pulse width of the signal at node (c) becomes. On the other hand, if the input signal (f) phase lags behind the signal at node (b), the signal at node (c) is a negative wave, and the less the signal (f) lags the signal at node (b), the narrower the pulse width of the signal at node (c). When the phase difference between the signal (f) and the signal at node (b) is quite small, the signal at node (c) is a very narrow impulse.

The phase comparator output signal at node (c) is preferably filtered through a low pass filter (404) and amplified by an amplifier (406) to generate a DC voltage signal to control the frequency of the output signal (nF) from voltage controlled oscillator (VCO) (408). The higher the DC voltage input into the VCO (408), the higher the frequency of the output signal of the VCD (nf) becomes, and, after feedback, the frequency at node (b) will be raised. On the other hand, if the DC voltage is negative, the frequency at node (b) will descend. Eventually, the phase of the signal (nf) will be stabilized to be similar to the signal at node (b). Furthermore, the frequency of the output signal (nf) which is n times the frequency f of the signal f (namely, nf) is then transmitted to ultra-high frequency counter (112) so that a high precision of the variation detected by the biosensor can be achieved. The operation principle of the combination of the phase lock loop (PLL) circuit with quartz crystal microbalance is further described below.

Essentially, the piezoelectric quartz crystal sensor (102) utilizes oscillation to detect and identify the mass variation of target materials, so it intrinsically is an oscillator. The oscillation is converted into pulses by oscillator circuit (102) and phase lock loop (110). The number of the pulses are counted by a counter (112). In the example 1 described below, an oscillation with frequency (f) of 10 MHz is adopted for the purpose of illustration. About 10,000,000 pulses are counted in one second. However, the last pulse, in fact, is not a complete pulse. Therefore, the actual count should be about 9,999,999 and ⅔ pulses. And yet, the highest resolution is 1 Hz, because such a decimal fraction cannot be directly detected by directly inputting the oscillation with frequency (f) into the counter.

The following examples are presented for illustration purposes and not to limit the scope of the invention.

EXAMPLE 1

Figure 7:
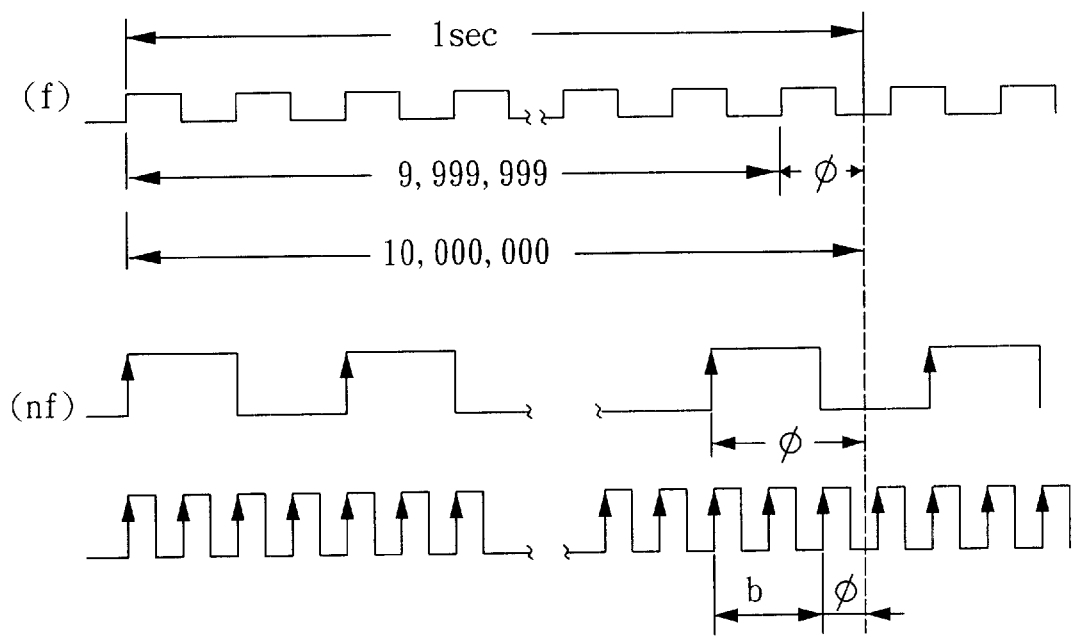
FIG. 7 illustrates the timing chart of an embodiment of the PLL circuit according to the present invention.

As illustrated in FIG. 7, if we incorporate and calculate the time of the last one pulse, φ, then we can raise the resolution of the bio-sensor. This invention employs the PLL circuit to achieve said purpose. The PLL circuit (110) is used to produce a signal with the same phase as the original signal, but the frequency thereof has been raised n times in a cycle. As shown in FIG. 7, if the original frequency f equals "a+φ", and "a" is an integer, since φ<1, the detectable frequency f is "a". Now we raise the frequency by n times, nf, nf=na+b+φ', wherein b=φ−φ'and is an integer. So, if "na+b" can be detected but φ', which is less than 1, cannot be detected, (nf) will be "na+b". If nF is divided by n, then we can get the original frequency f, (na +b)/ n=a+(b/n). Therefore, we get the frequency count number of "a+(b/n)". In other words, the resolution has been raised n times.

On the other hand, since the PLL circuit (110) comprises a filter (404) to trace the phase error and employs a closed loop control to retain the phase, even if the input signal is affected by noise that results in frequency jittering, the PLL circuit will not produce any instantaneous change, and a stable result can therefore be achieved. Such a result is an extraordinary and unexpected advantage of using a PLL circuit.

FIG. 3 shows details of an implementation of the circuit of FIG. 2 in which the signal sensing circuit includes a central processing unit (318), data recorder (320), corresponding level and tn-state converters (324, 326, 328, and 330), latches (322, 334), clock (336), and an RS232 interface (338). The signal frequency (f) of the oscillator (304) connected to chip (302) is input through a signal receiver (314) to PLL circuit (310), which generates an output with an n times frequency (nf). The signal nf is sent to an ultra-high frequency counter (312) before being level converted by converter (324) and applied to counter (306). The ultra-high frequency counter (312) counts the number of pulses produced in every second, and thus a resolution of 1/n can be achieved . For instance, if n=100, the resolution will be 0.01. Since the present invention employs hardware to implement the high speed sampling, the variation sensed by of biosensor can be rapidly and precisely measured. Because the division of frequency (nf) by n results in the frequency of the signal at node (b), which is then used in phase comparison, an output frequency (nf) which is n times the input frequency (f) can finally be obtained, and the phase difference between (f) and (nf) is a fixed value, Z, as shown in FIG. 6.

Furthermore, as illustrated in FIG 4, the low pass filter (404) may not only make the pulse width at node (c) correspond to the DC voltage at node (d), but also eliminate the noise. Therefore, the output of PLL possesses a merit of quite small jittering. Such a merit may overcome the problem of getting a worse S/N ratio after raising the resolution. This is an extraordinary advantage.

The above description fully discloses the invention including preferred embodiments thereof. Modifications and improvements of the embodiments specifically disclosed herein are within the scope of the following claims. Without further elaboration, it is believed that one skilled in the area can, using the preceding description, utilize the present invention to its fullest extent. Therefore, the examples herein are to be construed as merely illustrative and not a limitation of the scope of the present invention in any way. The embodiments of the invention in which an exclusive property or privilege is claimed are defined as follows.

What is claimed is:

1. A high resolution biosensing system for detecting and identifying a biochemical material to be tested by using a proportional relationship between frequency variation of oscillation and mass of the biochemical material to be tested, comprising:

a biosensor for sensing mass of the biochemical material to be tested;

an oscillator made of piezoelectric material and arranged to generate oscillation based on the sensed mass of the biochemical material to be tested;

a frequency multiplication circuit, including a phase-lock loop circuit for receiving the oscillation of the oscillator and generating pulse signals;

an ultra-high frequency counter for counting the pulse signals from the phase-lock loop circuit; and a microprocessor and interface circuits for storing and controlling output from the ultra-high frequency counter, wherein said phase-lock loop circuit generates pulse signals having a frequency which is n times a frequency of the oscillator and a constant phase difference relative to the oscillation, where n is a natural number greater than or equal to 1, to trigger the ultra-high frequency counter.

2. The high resolution biosensing system as claimed in claim 1, wherein the sensitivity of the biosensing system is above $10^{-10}$g.

* * * * *